(12) United States Patent
Terranova et al.

(10) Patent No.: US 9,474,651 B2
(45) Date of Patent: Oct. 25, 2016

(54) DETACHABLE WELDING FACE MASK

(71) Applicants: MaryAnn Terranova, Greenfield Center, NY (US); Stephen James, Saratoga Springs, NY (US)

(72) Inventors: MaryAnn Terranova, Greenfield Center, NY (US); Stephen James, Saratoga Springs, NY (US)

( * ) Notice: Subject to any disclaimer, the term of this patent is extended or adjusted under 35 U.S.C. 154(b) by 74 days.

(21) Appl. No.: 14/301,744

(22) Filed: Jun. 11, 2014

(65) Prior Publication Data

US 2015/0359678 A1 Dec. 17, 2015

Related U.S. Application Data

(60) Provisional application No. 62/010,478, filed on Jun. 11, 2014.

(51) Int. Cl.
*A61F 9/06* (2006.01)
(52) U.S. Cl.
CPC .................................. *A61F 9/061* (2013.01)
(58) Field of Classification Search
CPC ........... A61F 9/06; A61F 9/064; A61F 9/061
See application file for complete search history.

(56) References Cited

U.S. PATENT DOCUMENTS

| | | | | | |
|---|---|---|---|---|---|
| 1,166,977 | A | * | 1/1916 | Favary | A61F 9/06 2/11 |
| 1,370,121 | A | * | 3/1921 | King | A61F 9/06 2/11 |
| 1,472,134 | A | * | 10/1923 | Peterson | A61F 9/06 2/11 |
| 1,893,617 | A | * | 1/1933 | Flood | A61F 9/06 2/11 |
| 2,167,969 | A | * | 8/1939 | Bowers | A61F 9/06 2/8.1 |
| 2,425,690 | A | * | 8/1947 | Strong | A61F 9/06 2/8.1 |

FOREIGN PATENT DOCUMENTS

DE 3616219 A1 * 11/1987 ............... A61F 9/06

* cited by examiner

*Primary Examiner* — Anna Kinsaul
(74) *Attorney, Agent, or Firm* — Cowan, Liebowitz & Latman, P.C.

(57) ABSTRACT

A welder's protective helmet is provided with a detachable face mask with a handle which allows the welder to detach the same, as desired, and hold the face mask in front of his/her eyes during welding but to easily and quickly move the same to the side for direct viewing. The handle can be provided with a forwardly directed V-shaped trough for holding the extension of the welding torch so that welding proceeds while the user's eyes are protected since the user's hand is holding both the welding torch in the trough of the handle which is also holding the face mask.

11 Claims, 8 Drawing Sheets

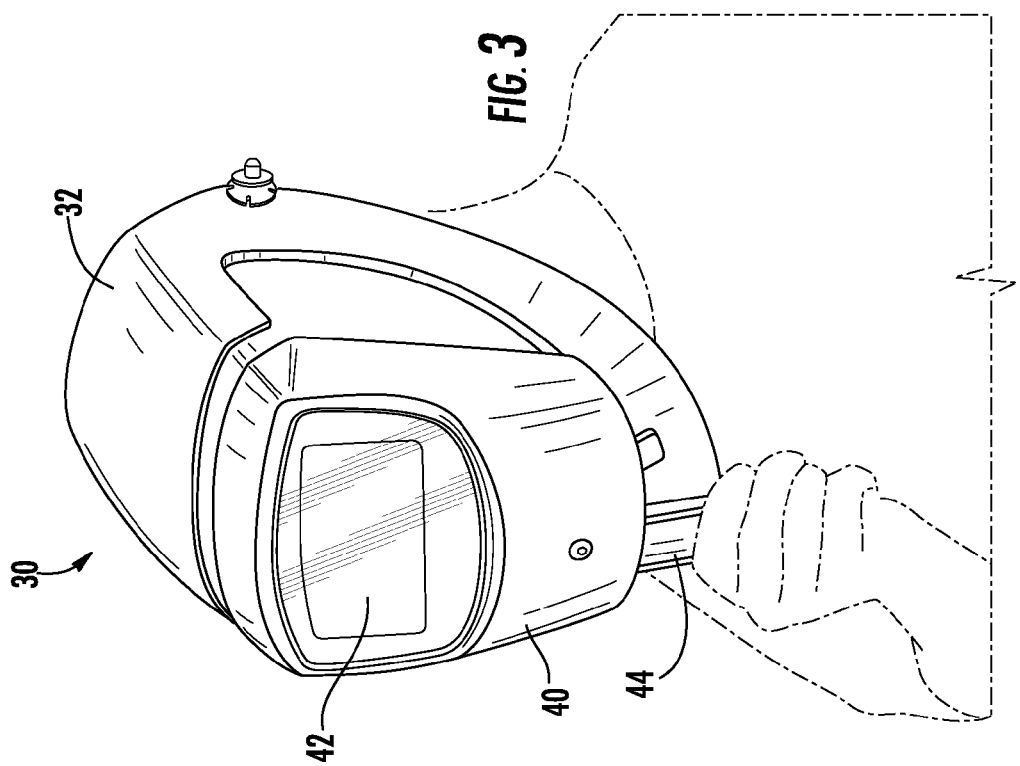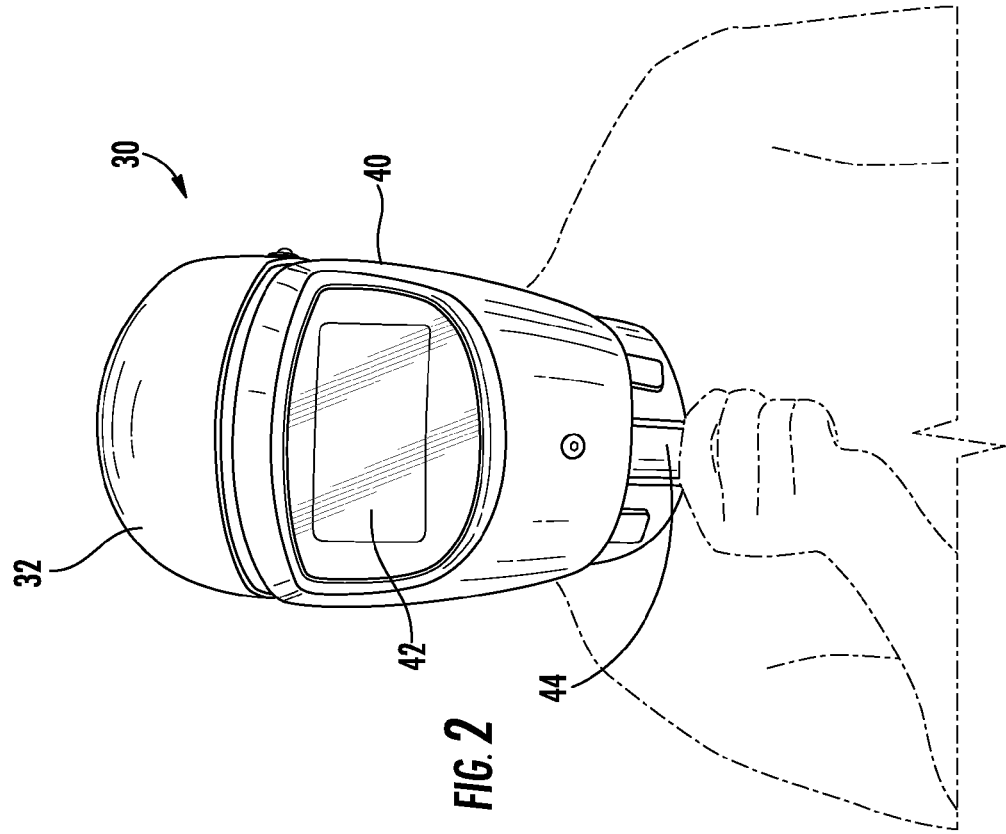

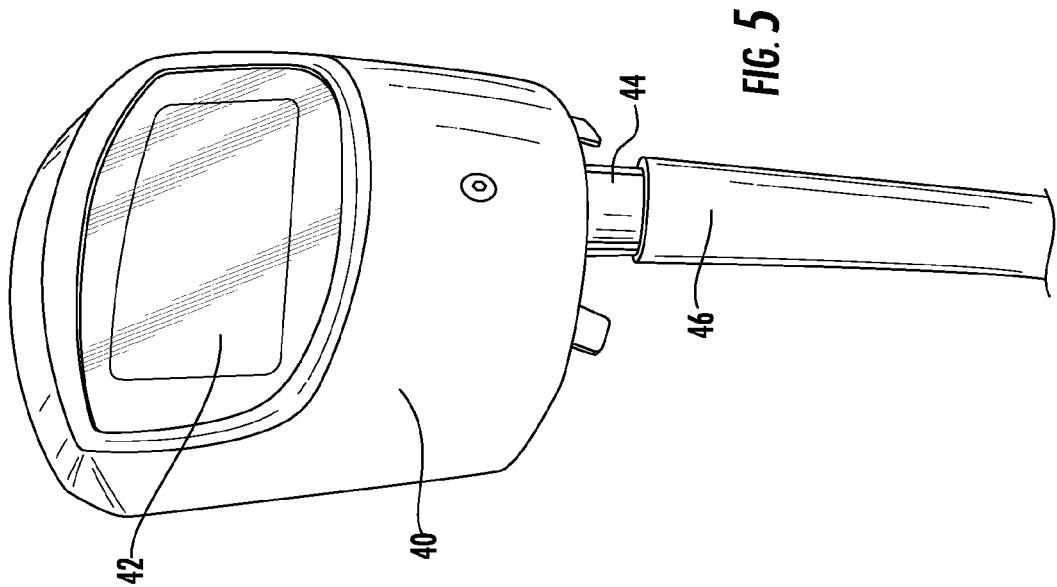
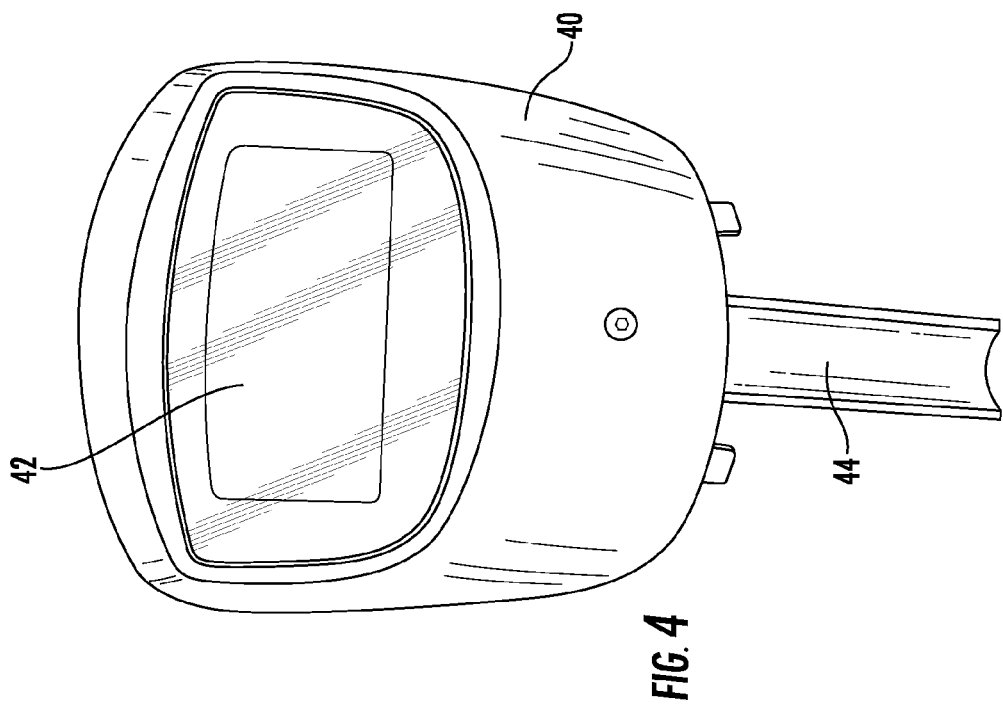

DETACHABLE WELDING FACE MASK

BACKGROUND OF THE INVENTION AND DISCLOSURE

The present invention relates to a selectively detachable face mask for a protective helmet to be worn while welding or, in another embodiment, a face shield useful for welding. Specifically, the present invention comprises a face covering component which is selectively securable to and detachable from a head covering helmet. The hand-held face protective component allows the user to quickly weld with the unit held by hand, not as a component of a helmet on the head, in front of the face (for protection) and then allows the user to easily and quickly move the protective component aside so that the user can see the progress of the weld without the mask being flipped up for viewing when a helmet is used. Also, the detachable and securable to a helmet, face mask, hand held by the welder, is provided with a V-shaped, forwardly directed groove or vertical trough which is adapted to hold the welding torch's supply line so that the welding operation is still simple even though the welder is using one hand to hold the mask (unlike the conventional welding mask which is on a helmet secured to the head and flips up, by hand, and down by either hand or a head-jerking motion).

Welding is a process of joining metals, often the same metal, sometimes different metals. Welding is accomplished by heating the metal to a high temperature so that the edges thereof sought to be joined become pliable and then holding them (sometimes under pressure) together during cooling. Welding is often done by melting the work pieces and adding a filler material to form a pool of molten material (the weld pool) so that when it cools a strong joint results. Often pressure is used in conjunction with heat to produce the weld. This is in contrast with soldering and brazing which involve melting a lower-melting-point material between the work pieces to form a bond between them, without melting the work pieces. Often a flux material is used to facilitate the joining of the work pieces, the formation of a weld and the ultimate strength of the new joint. The welding process, in essence, employs a torch, powered by a gas, which can produce a very high temperature flame for heating the metallic work pieces and the material used for the weld, whether the same material, a flux material or a different material. After they become attached, after the temperature of the separate pieces are raised to the molten/pliable range, the pressure of one piece to the other and then the consequent cooling causes the edges to cool and a secure and strong joint is formed between the work pieces. To accomplish the melting process of the metals and to raise the temperature of the materials to the molten level, users employ blowtorches, laser beams, or other oxy-acetylene torches and welding tools which are adapted to provide a source of high temperatures—those required for formation of welded joints in metals.

Because of the risk to the eyes, of burns and other injuries which could occur during use of those high temperature sources, the oxidation of flux, the arc of welding, etc., safety precautions are often taken to protect the hands, clothes, and especially the face and eyes of the welders. These protective devices include the use of heavy leather gloves, protective long sleeves to avoid direct exposure to the skin, and goggles or welding helmets to protect the head, face and eyes from burns, bright light, and/or ultraviolet light and the spark of the arc of welding.

Welding helmets are commonplace and often used. These often comprise a see-through protective glass-like face plate which protects the eyes from UV rays and allows the welder to see the welding and the joint, during the process. Yet, to see the joint clearly, the welder often needs to remove the protective face mask. The conventional face masks and helmets are integrated and the face mask hinged so that it covers the face during welding but can be manually and quickly hand flipped upwardly for viewing the weld. Then, if additional welding is required, the face mask can be manually flipped back down, into the face and eye protecting position, or, more experienced welders can quickly jerk or nod their head to cause the face mask to flip from the up position to the face protecting position. Each time the welder desires to clearly and closely view the weld joint, however, the welder must manually flip the face mask upwardly and each time the welder desires to continue to weld a joint, the face mask must be flipped downwardly, manually or by the jerking of the head. This can be tedious and time consuming.

Conventional welding helmets incorporate a horizontally extending hinge mechanism rotatively securing the face plate to the front opening of the helmet. The bulk of the helmet is adapted to sit upon and around the head of the user, in the nature of a motorcycle, hockey goalie or bobsled-like helmet. The hinge mechanism for the face plate allows the welder/user to lift up the face plate portion of the helmet when he ceases to use the blowtorch or other tool and when the risk of injury has temporary dissipated so that the joint can be inspected without the face mask blocking the line of sight.

Thus, it is believed highly desirable to provide a welding helmet for protection of the top, sides and back of the welder's head and also including a mechanism for protecting the face and the eyes of the welder. Yet, it is desirable for the welder to be able to quickly view the weld and then go back to welding, without manually flipping the face plate, or doing the same by jerking the head. Elimination of the manual flipping up of the face plate each time a weld is sought to be viewed and then flipping the same down into position, can be tedious and, yet, the direct line of sight is important to inspect the weld as is the protection of the eyes, when welding is being done. Thus, a face plate component which is entirely detachable and easily reattachable to the helmet would seem to satisfy the welder's needs. It would allow the welder to operate in the welding mode, with face covered and eyes protected, allow the welder to inspect the weld, as desired, by flipping up (and then back down) after a weld operation is done, and, in addition, it would allow the separation of the mask from the helmet so that the welder can quickly and easily continue to weld, with eyes protected by having the mask held by hand in front of the eyes and, yet, when the weld is needed to be inspected, the welder can easily move the mask aside or more his head to the side, for direct viewing of the weld.

In addition, however, since the present invention contemplates that the welder's hand (at least one) be used for holding the removable face plate, the present invention contemplates that the handle for the same be provided with a V-shaped vertical notch, trough or channel for locating the extension of the welding torch therein so that the welder, while holding the face plate is also simply holding the extension of the welding torch as the latter fits conveniently within the V-shaped channel or trough of the handle. In this manner, the welder can quickly form a weld, looking through the protective face plate, while holding the handle for the same with the welding torch held within the V-shaped groove or channel therein, and, then, for inspection of the weld, the face plate is simply laterally moved away from the eyes and the welder has a clear and direct line of sight to the weld, When further welding is required, the welder can move the face mask and the welding torch back into position, protecting the face and eyes of the same. This simple back and forth of the movement of the detachable face mask i.e., from in front of the eyes during welding to aside during inspection of the weld is far easier and quicker for a welder than the flip up and down of the current integrated masks of welding helmets. Also, as mentioned, the V-shaped channel of the handle of the current invention allows for one hand to be dedicated to the movement of the face plate as the same hand is holding the handle and the welding torch rod-like extension.

In an alternate embodiment of the invention, the handle for the mask is provided with a bendable (yet strong) connection to the base of the face mask so that it can be easily adjusted into a precise orientation (and held there by the secure yet bendable connection). This promotes comfort and ease of use.

DESCRIPTION OF THE PRIOR ART

To the Applicants' knowledge, no prior art welding helmets comprise a fully detachable and yet easily securable protective eye and face plate component with a downwardly extending hand-holding handle. No prior art welding helmet provides a simple removable face place with a handle which will, when attached to the helmet portion, fully protect the user's face from the hazards associated with welding. Some prior art welding helmets provide an upwardly and hingedly connected face plate which allows the face plate to be moved out of the line of sight but requires either a manual movement or a head jerk, a forceful nodding to place the face plate in a protecting of the face and eyes position. Other prior art welding helmets do not offer any maneuverability of the face plate, thus requiring the welding helmet to be fully removed from the head to remove the obstruction of a mask or tinted viewing window otherwise in the user's line of sight. This is not desirable because a welder generally wears thick rubber gloves which make it more difficult to accurately place a helmet on and clumsy to remove and because the necessity of a welder to inspect the weld, during its formation, is important and requires, often, many and frequent steps of welding, inspection, welding, inspection, etc. Thus, total removal of the helmet is time consuming.

The present invention discloses a welding helmet comprising a head (top of head, sides and back of head) covering component and an easily securable and yet simply detachable face plate component. According to the invention, the face plate is provided with a downwardly extending handle which allows the user to easily grasp and use the same, whether as a protective mask during welding or to hold the same aside so that the welder can inspect the weld. Also, the handle is provided, preferably, with forward projecting, vertical trough for holding the welding torch therein which trough makes the holding of the face mask a simple matter, since the welder needs to hold the welding torch extension anyway.

The present invention provides a new and improved welding helmet which allows a user to protect his face during a welding process, but to fully remove the face plate during certain finishing welding operations. This allows the user/welder to weld with the face plate held by itself in between the eyes and the arc and secured to the helmet, and, yet, when nearing completion, the face mask can be removed from the helmet and manually held, allowing for the continuation of welding and the periodic inspection of the same. For inspection, the face plate can be laterally moved aside. The downwardly extending handle allows the welder to simply and quickly move the face plate into position for additional welding and out of face and eye-blocking position for a direct inspection. The face plate is held by a downwardly extending projection or handle from the base of the face mask. Preferably, the handle is provided with a V-shaped channel or groove, facing forwardly, which locates and holds the welding torch's extension piece, near the nozzle, so that a single hand can be used for both holding the face mask during welding and for directing the tip of the nozzle towards the metal pieces for welding.

In between welding, when the user desires to see the joint being formed and the materials being welded, without the face plate obstructing his line of sight, the face plate is simply moved aside (along with the torch) or the welder's head moved to the side to have a direct line of sight to the weld being formed.

SUMMARY OF THE INVENTION

The present invention comprises a new welding helmet comprising a head covering component and a detachable and easily reattachable face plate. The face place is provided with a handle and the handle has a forwardly projecting trough for holding the line extension of the torch therein (the line is generally a hose so the circular cross section of the hose fits nicely within the semi-circular trough of the handle). The handle allows the easy holding of the face mask between the welder's eyes and the weld being formed. It also allows the face mask to move by hand to a position so that the welder/user can have a direct line of sight to the formed weld. Alternatively, the present invention comprises only the face mask, with a downwardly projecting handle having a trough for holding the line extension of the welding torch.

The head covering component preferably comprises a conventional set of adjustable head covering and engaging pieces and/or a set of straps to hold the same comfortably in place on and around the top of the head of a wearer during use. The face plate is securable to the otherwise forwardly open, head-covering component by means of a securement mechanism, preferably a set of snaps, a set of hooks and loops (Velcro®) or other known mechanical securement means, which allows the face plate to be quickly and easily removed from the front opening and reinstalled, as desired. Preferably, the holding and mask removal mechanism will still allow the helmet and face mask to operate quite conventionally, i.e., face mask down during welding, flippable up when inspection of the weld is desired, and then flipped down for additional welding, whether by a jerking of the head down or by manual placement of the face plate or mask into position. Yet, the ability of the face mask to be separated and held in a hand provides great versatility to the welder for further welding, allowing the welder to make additional welds and, yet, in an instant allowing the welder to quickly and easily move it aside (or one's head, respectively) for a direct line of sight view of the weld.

The present invention contemplates that the face plate may be removed during welding and allows the welder to quickly weld and inspect by moving the face plate, held in the hand, from in front of the eyes to aside the face and head. This allows welding and viewing quickly and easily. For more lengthy welding times, the face plate can be secured to the front of the helmet and a hinge can be provided for conventionally flipping the face plate from a down position for welding to an up position for inspection. Further welding can be done by flipping the face mask down to protect the face by jerking or snapping the face mask into position, causing the same to rotate about its hinged, or a simple manual movement of the face mask back down to cover the front of the mask.

The improvement, here, however, is providing a detachable face plate, held by a handle in the welder's hand (or a stand into which the face plate can be secured) which allows the welder's eye's and face to be protected during welding by placing it between the arc of the torch and the wearer's face and eyes and, yet, allows the welder's eyes and face to be quickly and simply moved laterally or the face plate moved laterally, relative to the welder, for inspection of the weld. And, if the face mask is separated from the rest of the helmet, the mask serves the dual function of holding, in a convenient manner, the extension pipe of the welding tool.

According to the present invention, the face mask is provided with a downwardly extending handle to facilitate the rapid movement of the face protector from in front of the face to the side. And, that handle is provided with a V-shaped groove or vertical, forwardly projected channel or trough to facilitate the holding of the face plate and the welding torch, in the same hand. According to another aspect of the present invention, the handle is secured to the base of the face mask by a flexible holder which is strong enough to hold the mask in position when the handle is held and, yet, allows the user to adjust the angle of the face mask to the handle, with the connection holding that angle until moved to a new or different angle.

BRIEF DESCRIPTION OF THE DRAWINGS

FIG. 2 is a front elevational view of the present invention, an over the head welding helmet with detachable face plate, showing the face plate attached to the helmet and with the face plate held in position by a welder's hand holding a downwardly extending handle;

FIG. 3 is a front and side perspective view of the present invention as shown in FIG. 2;

FIG. 4 is a front elevational view of the face plate component of the present invention after it has been removed from the front of the welding helmet;

FIG. 5 is a front perspective view of the face plate component shown in FIG. 4, and showing the welder's hand on the handle of the face plate component for holding and removing of the same from the helmet and showing a tube or pipe representative of the line extension for the torch held in the vertical groove or trough of the handle in the hand of the welder;

DETAILED DESCRIPTION OF THE DRAWINGS AND THE PREFERRED EMBODIMENT

Description will now be given of the invention with reference to the attached FIGS. 1-10. It should be understood that these Figures are exemplary in nature and in no way serve to limit the scope of the invention.

Figure 1:
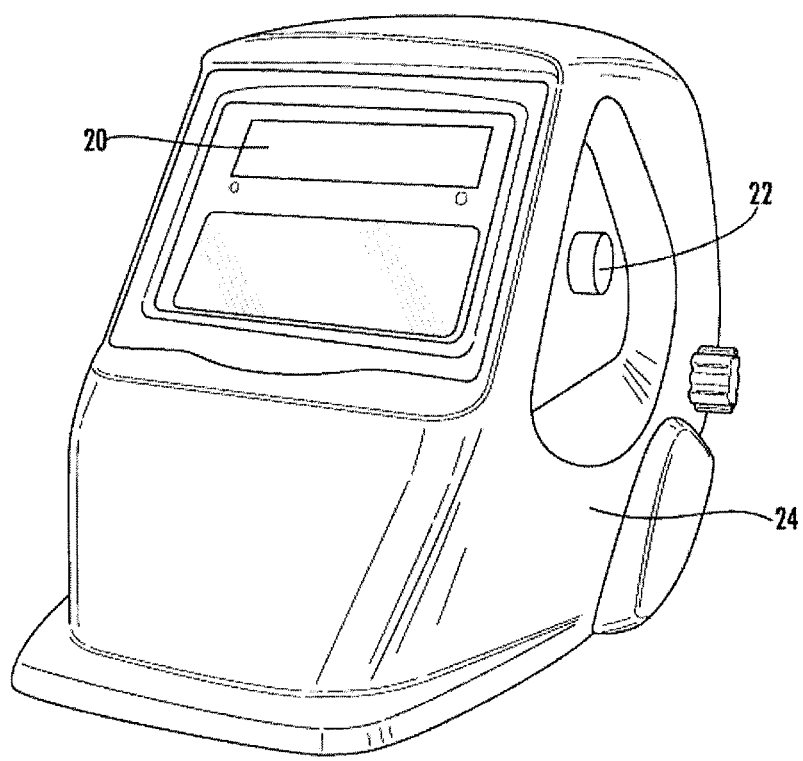
FIG. 1 is a front and side perspective view of a prior art welding helmet with hinged eye protective portion.

As can be seen in FIG. 1, commonly known prior art welding helmets generally comprise a face covering component 20 which is permanently yet hingedly secured to helmet 24. These prior art helmets allow for the face covering component 20 to be selectively moved up and away, through a horizontal hinge, from the face of a user by means of side knob 22 connected to the face covering component 20. As the knob 22 turns, the face mask rotates about the hinge, not shown, up and above the top of the helmet or down, so that the protective screen 23 is in front of the wearer's eyes. As can be seen, the protective screen 23 is part of the front face plate of the prior art helmet and that face plate is an integral component of the helmet. When the face plate is aligned with the wearer's eyes and between the high light intensity of a welding torch and the eyes of the welder, the face plate protects the same from the bright light of the arc and, yet, allows for the welder to basically see the welding location. The protective screen 23 is preferably made of a somewhat translucent material, likely thick blue tinted glass, to allow the welder to see and to see the arc of the welding operation and, yet, the brightness of the arc of the weld is subdued by the screen. When the welding is finished or the weld needs to be inspected, the welder will turn off or stow the welding torch on a stand or easel and flip the protective screen 23 upwardly, either by manually turning the knob 22, or lifting up the bottom edge of the hinged protective screen. After inspection, if further welding is required, the user can re-locate the protective screen by quickly jerking or nodding the head forwardly, so that the protective screen 23 is in front of the eyes of the welder.

However, in the prior art device, the protective screen 23 cannot be removed from helmet 24. Thus, the only way of removing it for direct viewing of the weld is to either remove the helmet entirely or by rotating the knob 22. Then, when further welding is required, rotating the knob 22 to place the protective screen in front of the eyes is required or the welder may quickly nod his/her head downwardly and forwardly to cause the protective screen 23 to be placed in front of the helmet, covering the eyes.

The present invention avoids this and provides a far simpler and efficient manner of quickly transferring from welding (with eye protection) to direct weld viewing (without anything between the eyes and the weld) and back. The prior art device is inconvenient and difficult for quick switching between welding and inspecting/viewing.

Thus, the present invention discloses a new welding helmet 30 comprising a top, back and both sides of the head covering component 32 and a removable yet securable face plate 40. Alternatively, only the face plate 40 may be provided as a separate device when the "heavy" welding has been completed but there still remains some welding to be performed. As can be seen in FIGS. 2 and 3, face plate 40 is configured to be tightly (by an O-ring, for example) securable to and yet easily removable from the front opening of the head covering component 32.

FIG. 2 further depicts the head covering (or over-the-head) component 32 having a helmet shape.

When a long time welding operation is contemplated or for storage of the face mask and the head covering component as a single helmet, the user can secure and maintain the face plate 40 to the front of the helmet. The face plate 40 has, however, a see-through glass-like screen which allows the welder's eyes to see through the same and to accomplish the weld without damaging the eyes (the filter of the glass protects the UV light rays from damaging the user's eyes).

According to one aspect of the invention, the securement of the face plate to the front opening of the helmet can be by a single snap-on mechanism, balls and detents, or, for example, the top edge of the face plate can have a rounded horizontal rod which is captured and held by a concave and correspondingly shaped horizontally extending receptacle on the helmet. This receptacle allows the rod to snap fit into it and be held thereby and, yet, when desired to be removed, the rod of the face mask can be slipped out of the concave receptacle of the helmet. So, the helmet with hinged yet securely held protective face plate and screen operates much like that of the prior art welder's helmet. The user can flip the protective plate up, rotating the plate about the axis passing through the rod held in the receptacle, to hold and rotate the face plate out of the way for direct viewing. And, when further welding is desired, the user can rotate the protective face plate back into position, with the screen replaced back in front of the welder's eyes. This can be done by physical rotation of the face plate or, as mentioned, by a snapping forwardly of the head to cause the screen to rotatively hinge into position.

Alternatively to the holding and rotating mechanism of a rod and concave receptacle, the device could be provided with a set of ball detents attached to the sides of the helmet, spring biased outwardly, and a set of apertures on the removable face plate. The face plate can slide back and over the ball detents, pushing them inwardly towards one another, until they pop back, outwardly, by the spring bias, located in the apertures. The mechanical interaction of the ball detents on the helmet and apertures on the removable face plate (or vice versa) will hold the face plate to the helmet and allow for relative rotation of the face plate about a horizontal hinge. The ball detents and apertures (or another suitable hinging and rotating mechanism) will also allow the face plate to rotate up and out of the way for direct viewing and back into location for welding and eye protection. Face plate 40 comprises a viewing window 42 through which a user can see the arc of the weld and, yet, not suffer damage to the eyes. When the face plate 40 is connected to head covering component 32, the device operates as a conventional helmet whereupon the protective covering flips up and down to protect the eyes during welding and to allow the direct sight of the weld after the face plate and protective screen is removed from being between the eyes and the weld.

However, according to the present invention, the face plate can be removed from the head covering portion. Then, the helmet or head covering component still protects the top, back, and sides of the head of the welder but the eyes and face are protected by the now-separated face plate portion which will be held by a hand (or a separate stand, like an easel or microphone holder). In this manner, the welder can use the arc welder and the welder's eyes and face are protected and, yet, when the welding is complete, the user merely shifts his or her head to the side of the protective face plate (or the face plate is moved off of and aside the face) for direct viewing. No longer is the user required to flip up, manually or by nodding one's head rapidly, to change the helmet from direct viewing to welding position or vice versa. Rather, the removability of the face plate and protective screen from the other aspects of the helmet promotes a far more comfortable protective helmet and eye-protecting device.

The protective face plate is provided with a downwardly extending handle 44. Preferably, the handle can have one or more, laterally extending finger grooves on its back to facilitate the ease of holding the same by the hand/fingers of the welder. This allows the welder to quite easily hold the face plate in front of his eyes and to also remove the same from the eyes so that a direct line of sight to the weld can be established. The handle preferably is provided with a forwardly directed concave surface, a so-called "half pipe." This downwardly extending yet forwardly opening of concavity allows the welder apparatus, specifically the extension rod of the torch apparatus at the point before the same necks down to the nozzle, to be received therein and held securely. Stated differently, the cylindrical pipe of the torch is held within the half-pipe of the handle so that the user's single hand can hold the face plate and the welding pipe. In this manner, the same hand holding the face plate such that the user's eyes are protected is also holding the arc welding device, with the cylindrical length of a portion of the arc welder within the half pipe section of the face plate. The face plate is moved into eye protective position and out, for welding by the welder and when removed from the line of sight, the face plate and the welding pipe are relatively laterally moved so that the welder has a direct view of the weld.

Viewing window 42 is preferably tinted or provided with a protective coating to shield the user's eyes from any UV or other harmful rays or direct contact with the sparks of the welding process which can occur as a byproduct of high temperature welding. Because of the tint of the viewing window 42 which is configured to protect the eyes of a user but also may partially obstruct the user's vision when small pieces of metal are being welded or make sight slightly more difficult, it is highly desirable to be able to remove the face plate 40 for direct viewing of the weld.

Face plate 40 preferably comprises a handle 44 which is connected to the bottom edge and center of face plate 40 for ease of removal and reattachment of the face plate 40 to head covering component 32. By providing a detachable face plate 40 with a handle 44, a user can easily remove the face plate, maneuver it or place it down while easily being able to reattach the same when desired. The handle allows the welder to move the face plate relatively laterally (or the welder's head moved to the side) for viewing the weld directly and the simplicity of the device allows the welder to move his/her head back behind the protective viewing window for further welding, as desired. Handle 44 is also comfortable for a welder wearing thick rubber gloves during a welding process as it provides an easily graspable rear surface for the user, while maintaining the gloves on his hands, to hold the face plate 40 and even easily allows removal of the face plate from the helmet 30 when desired. As mentioned, the front of the handle is a hollow half pipe which easily accepts and holds the extension rod of the welding apparatus. It can be placed and held therein with the hand of the user holding the handle and the face mask and, in addition, the same hand holding the extension rod within the concavity of the handle. This is quite convenient. The user's hand will wrap around the rear of the handle and over the front of the handle, holding the extension pipe within the half pipe of the handle so that the handle and the extension pipe move as "one." This allows the welder to easily weld.

As can be seen in FIGS. 4 and 5, the face plate 40 of the present invention may be fully detachable from the head covering component 32 or it may be a separate device. A user can remove the face plate 40 by holding the handle 44 and pulling on the handle 44 so that the face plate 40 snaps off of, and dislodges from, the head covering component 32. Or the face plate, protective screen and handle are a separate and distinct tool for use by a welder. Relatedly, when a user wishes to reattach the face plate 40 to the head covering component 32, he can hold handle 44 and push face plate 40 back onto the head covering component 32 until it snaps into place. A variety of simple mechanical mechanisms can be used for securing and removing the face plate from the head covering component, all while allowing for selective rotation of the face plate with respect to the face of the user, in a conventional manner.

The face plate 40 and helmet are provided with any suitable mechanical securement means, whether a snap and snap receiver set of components, a piece of fabric surrounding the face opening with button holes to be secured to a corresponding piece of fabric on the face plate with buttons, hooks and eyelets, or other known means to selectively hold the face plate (and allow removal) of the face plate from the front of the helmet.

Figure 6:
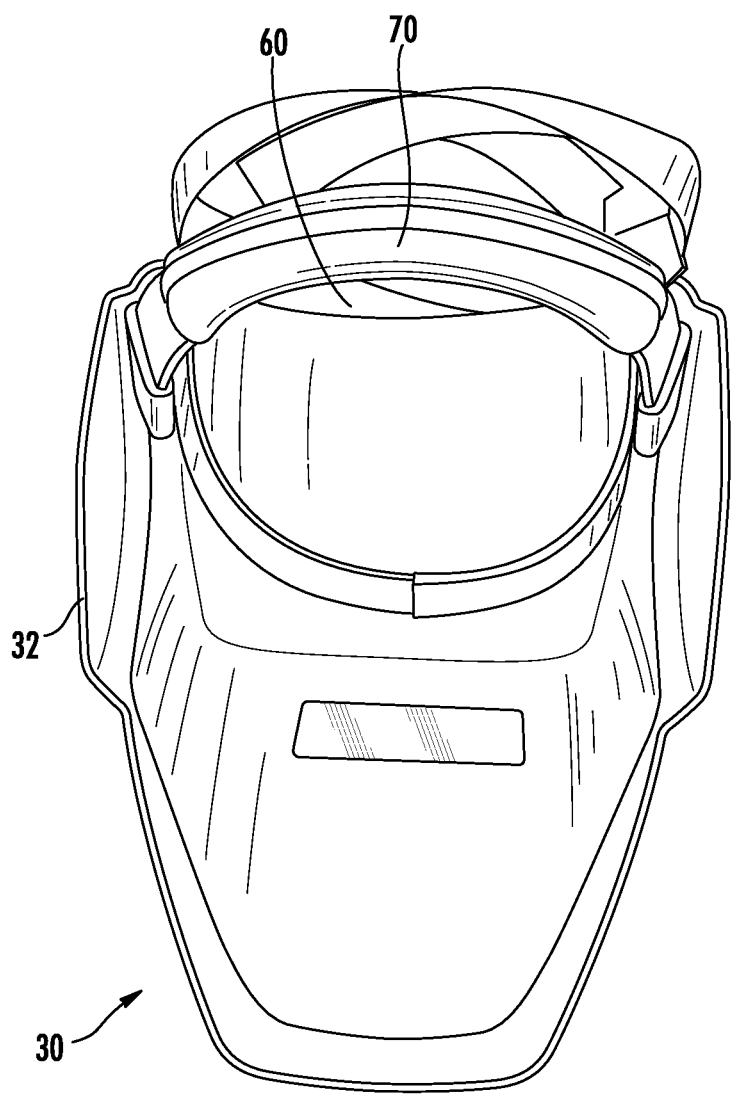
FIG. 6 is a rear elevational view of the present invention of the helmet.

FIG. 6 is a rear elevational view of welding helmet 30 and specifically of head covering component 32. Head covering component 32 comprises a diameter-adjustable head strap 70 which is configured to pass around and behind the forehead of a user (into chamber 60) and hold the welding helmet 30 in place on the user's head while in use, similar to a bicycle helmet, motorcycle helmet, ski helmet, fireman's hat, even a baseball helmet.

Figure 7:
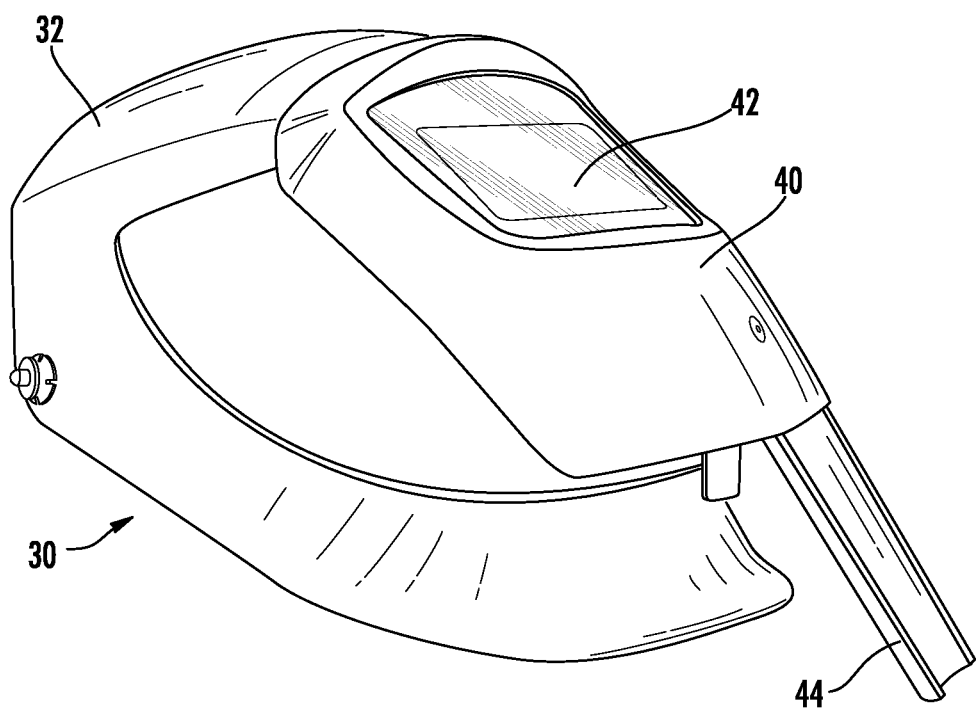
FIG. 7 is a side and front perspective view of the present invention similar to that shown in FIG. 3.

FIG. 7 is a front, top and side perspective view of the face mask and protective screen, with handle, of the present invention when integrated into a helmet 30. As can be seen therein, handle 44 is attached to central, bottom edge of face plate 40 and configured with a forwardly extending half-cylinder or trough. This allows the welding rod to be placed and held therein when the user holds the handle 44 and wraps his/her fingers therearound. Also, the rear and smooth cylindrical surface of the handle 44 allows for the comfortable holding of the handle when the face plate 40 is held.

In the preferred embodiment, the face mask or face plate is capable of being integrated into an overall protective helmet for welding. Selectively, however, the face plate can be rotated up and down during the welding operation. Also, however, according to the present invention, the face mask can be removed from the rest of the helmet and used as a separate tool, to allow the user to easily go from welding to inspection. The user will hold the handle during the operations of welding or inspection, or the face mask can be held in an easel or other support device.

Figure 8:
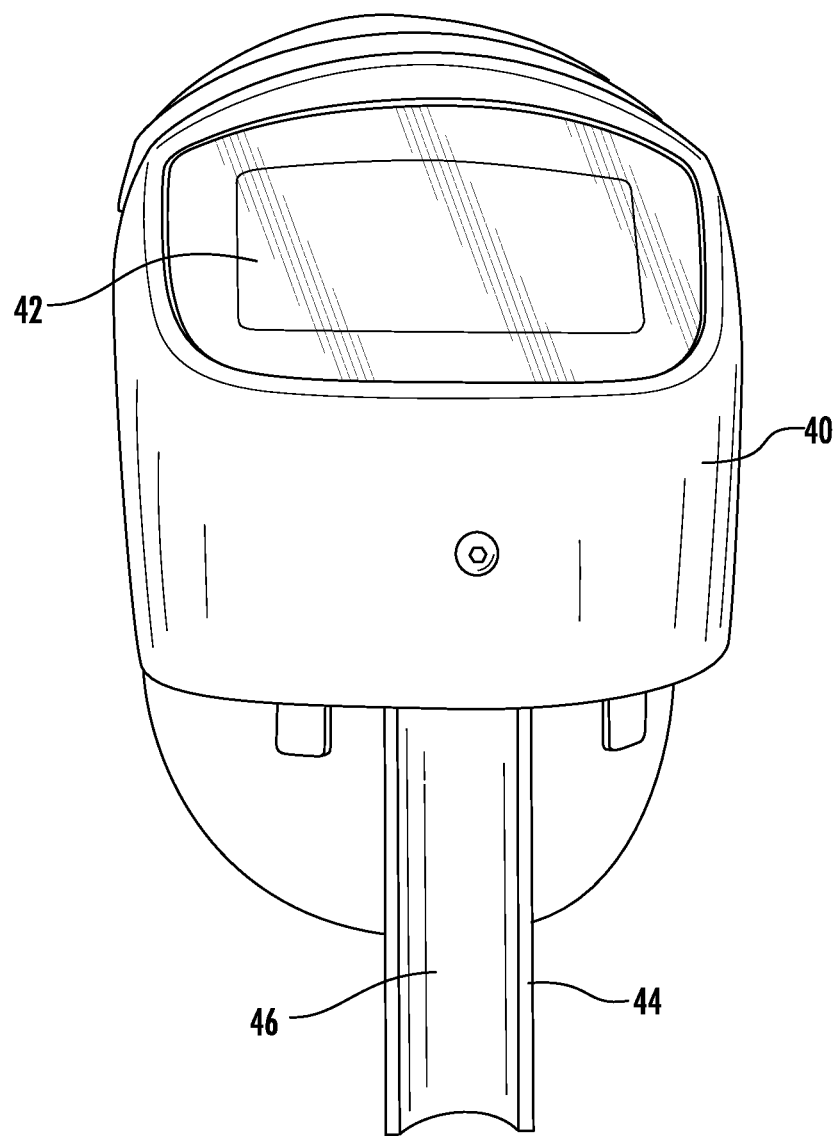
FIG. 8 is another front perspective view of the present invention, similar to that shown in FIGS. 3 and 4.

FIG. 8 shows the font of the device with the face mask having the downwardly extending handle. The handle is preferably provided with a forwardly projecting trough or half pipe for allowing holding of both the face mask and the welding torch by a single hand. This face mask can be a separate tool for use in welding or the device can be a component of an overall welder's helmet where the face mask and the balance of the helmet are capable of being integrated or separated, as desired.

Figure 9:
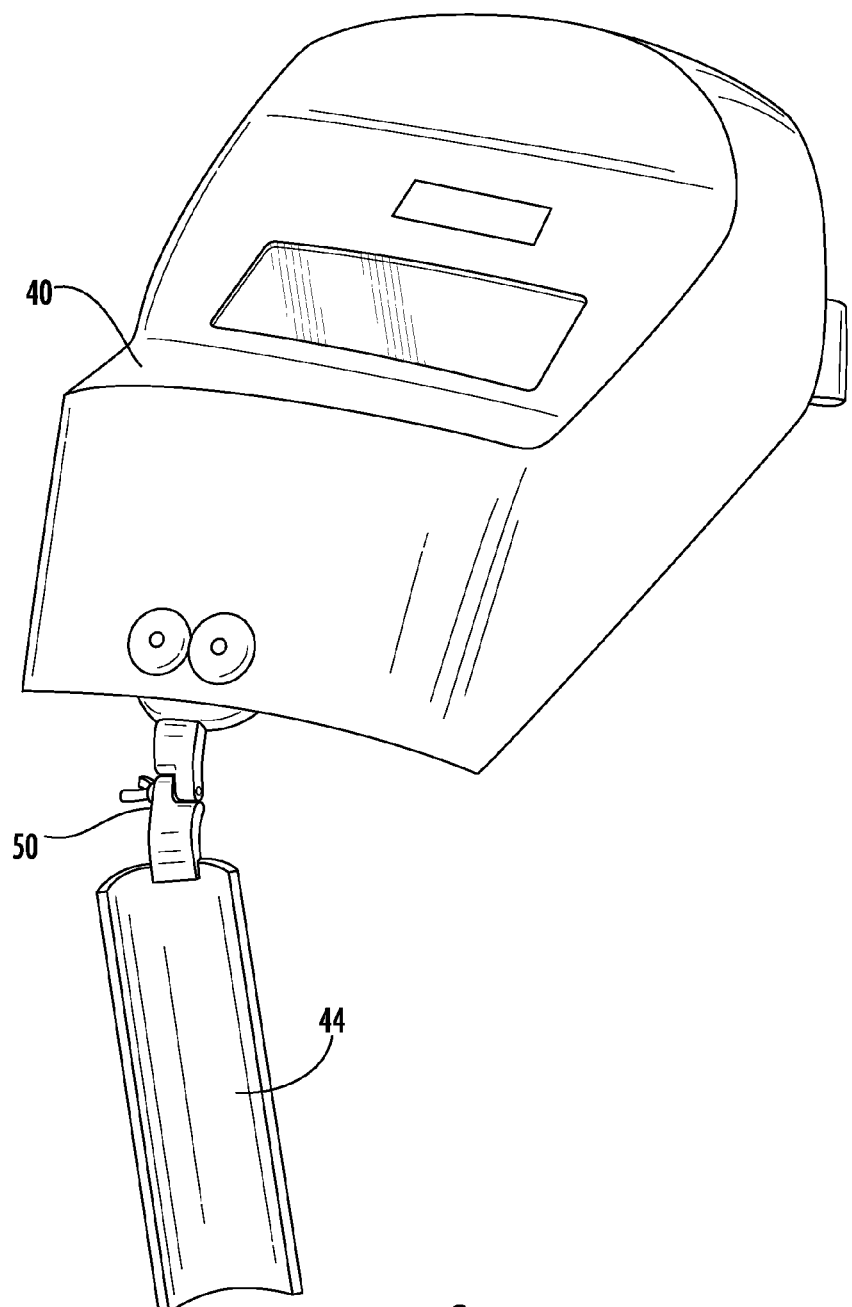
FIG. 9 is a front, top and perspective view of another embodiment of the present invention, the face mask component and handle, with the connection between the bottom of the shield of the face mask to the handle/extension holding trough, being a flexible connection.
Figure 10:
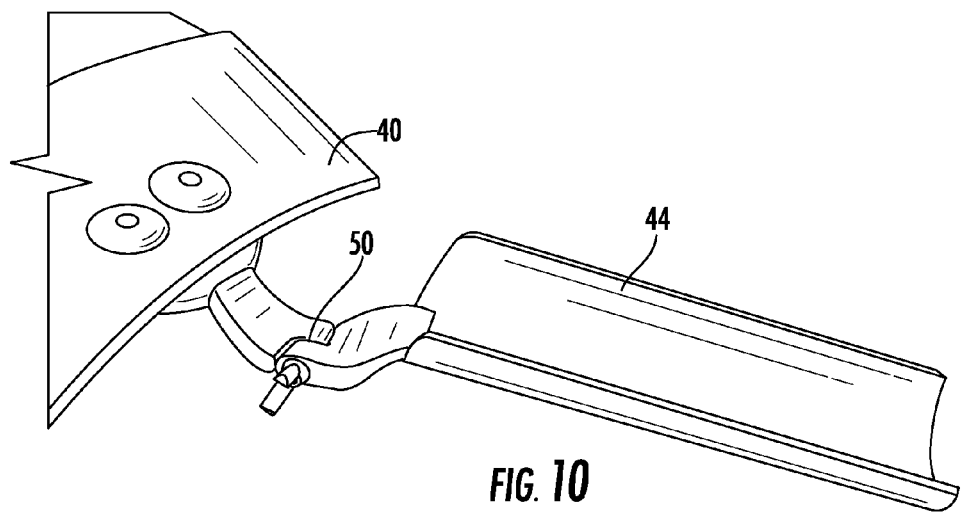
FIG. 10 is an enlarged perspective view of the present invention, shown in FIG. 9, and shows the flexible connection between the handle and the bottom of the face mask.

According to another embodiment of the invention, shown in FIGS. 9 and 10, the face mask or protective portion 40 of the device is secured to the handle 44 via a flexible connector 50. Flexible connector 50 is a firm and strong connection which allows for bending of the same to adjust the angle and orientation of the face mask with respect to the handle and that angle and orientation will "hold" until displaced to a new angle/orientation. The use of the bendable and strong-holding connector 50 is believed to provide a measure of comfort to the user so that the face mask can be conveniently and comfortably held in position by the hand on the handle 44 and yet the face mask can be removed, as desired for a direct line of sight to the weld, as desired.

It will be understood by those of ordinary skill in the art that various changes may be made and equivalents may be substituted for elements without departing from the scope of the invention. In addition, many modifications may be made to adapt a particular feature or material to the teachings of the invention without departing from the scope thereof. Therefore, it is intended that the invention not be limited to the particular embodiments disclosed, but that the invention will include all embodiments falling within the scope of the claims.

What is claimed:

1. A protective welding helmet comprising:
   a) an over-the-head component including substantially enclosing top and side portions, the over-the-head component being configured to be worn by a user and to protect the top and sides of the user's head;
   b) a face plate component having an eye-protective section, said face plate component being detachable from and reattachable to said over-the-head component,
   c) said face plate having a handle, such that when detached, said face plate, when held by said handle, is separate from said over-the-head component to allow the user to alternatively look through said eye-protective section and continue to perform a weld and to hold said face plate aside of the user's eyes to allow a direct line of sight to said weld,
   wherein:
   the handle is secured to the face plate component using a flexible connector, the handle having a convex surface and an opposing concave surface forming a holding trough for holding at least one of a handle of a welding torch and a line extension of the welding torch,
   the convex surface of the handle is configured to face toward the user's body when the face plate component covers the user's face and the concave surface of the trough is configured to face away from the user's body when the face plate component covers the user's face, and
   the flexible connector includes a first end directly coupled to the face plate component and a second end directly coupled to the handle, and the flexible connector is bendable so as to allow adjustment of an angle and orientation of the face plate component with respect to the handle.

2. A protective welding helmet as claimed in claim 1 wherein said holding trough is V-shaped.

3. A protective face covering plate for use in welding comprising;
   an eye protective section configured to be positioned relative to a user to separate and to protect the user's eyes from a weld in progress; and
   a handle secured to said face covering plate using a flexible connector, the handle having a convex surface and an opposing concave surface forming a trough for holding at least one of a handle of a welding torch and a line extension of the welding torch;
   wherein the convex surface of the handle is configured to face toward the user's body when the face covering plate covers the user's face and the concave surface of the trough is configured to face away from the user's body when the face covering plate covers the user's face, and
   wherein the flexible connector includes a first end directly coupled to the face covering plate and a second end directly coupled to the handle, and the flexible connector is bendable so as to allow adjustment of an angle and orientation of the face covering plate with respect to the handle of the face covering plate.

4. A protective face covering plate for use in welding as claimed in claim 3 wherein said handle is secured to a central bottom edge of said face plate.

5. A protective face covering plate for use in welding as claimed in claim 3 further comprising a mechanical coupling for securing and to allow easy removal of said protective face plate from an over-the-head helmet.

6. A protective face covering plate for use in welding as claimed in claim 5 wherein said mechanical coupling comprises a horizontal hinge element such that said face plate is configured to be flipped up and down as desired, when the user desires a direct line of sight to said weld and for further welding, respectively.

7. A protective face covering plate for use in welding as claimed in claim 3 wherein the width of said eye protective section is configured to extend across the face of the user.

8. A protective welding helmet as claimed in claim 1 wherein when said face plate component is attached to the over-the-head component, the face plate component is rotatable in an upward direction relative to the over-the-head component and configured to expose the user's eyes.

9. A protective welding helmet as claimed in claim 1 wherein said over-the-head component has a helmet shape.

10. A protective welding helmet as claimed in claim 1, wherein the face plate component includes a front surface configured to face away from the user's face when the face plate component is positioned to cover the user's face, and an opposing back surface configured to face toward the user when the face plate component is positioned to cover the user's face, and wherein the first end of the flexible connector is coupled to the back surface of the face plate component.

11. A protective face covering plate for use in welding as claimed in claim 3, wherein the face covering plate includes a front surface configured to face away from the user's face when the face covering plate is positioned to cover the user's face, and an opposing back surface configured to face toward the user when the face covering plate is positioned to cover the user's face, and wherein the first end of the flexible connector is coupled to the back surface of the face covering plate.

* * * * *